United States Patent [19]
Crosby et al.

[11] 3,974,299
[45] Aug. 10, 1976

[54] IONIC SWEETENER

[75] Inventors: Guy A. Crosby; Grant E. Dubois; Ned M. Weinshenker, all of Palo Alto, Calif.

[73] Assignee: Dynapol, Palo Alto, Calif.

[22] Filed: Mar. 24, 1975

[21] Appl. No.: 561,522

Related U.S. Application Data

[63] Continuation-in-part of Ser. No. 486,282, July 8, 1974, abandoned.

[52] U.S. Cl............................. 426/548; 260/503; 260/511; 260/429 R; 260/429.9; 260/438.1; 260/439 R; 260/448 R
[51] Int. Cl.² .......................................... A23L 1/22
[58] Field of Search............... 260/503, 511, 429 R, 260/429.9, 439 R, 438.1, 448 R; 426/548

[56] References Cited
UNITED STATES PATENTS

| | | | |
|---|---|---|---|
| 3,739,064 | 6/1973 | Rizzi | 426/548 X |
| 3,751,270 | 8/1973 | Rizzi | 426/548 |

FOREIGN PATENTS OR APPLICATIONS

C1196  1/1973  Hungary

Primary Examiner—A. Louis Monacell
Assistant Examiner—Esther L. Massung
Attorney, Agent, or Firm—William H. Benz

[57] ABSTRACT

A group of novel dihydrochalcone compounds represented by the formula

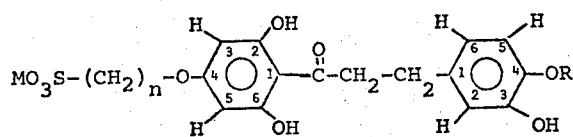

wherein $R$ is a lower alkyl or from one to three carbon atoms inclusive, $n$ is an integer of from one to three inclusive and $M$ is a physiologically acceptable metal cation, are disclosed. These materials are useful as dietetic sweeteners.

17 Claims, No Drawings

IONIC SWEETENER

REFERENCE TO RELATED APPLICATION

This is a continuation-in-part of copending U.S. patent application Ser. No. 486,282, filed July 8, 1974.

BACKGROUND OF THE INVENTION

Field of the Invention

This invention relates to new ionic dihydrochalcone compounds and to consumable materials such as foods sweetened by the addition of these compounds.

The Prior Art

There is a trend toward the use of more and more sweetening by the world's population. Primarily, this sweetening is obtained from sucrose. Sucrose has several medical disadvantages, including high caloric content, which promotes obesity; ability to cause dental caries; and non-tolerance by diabetics. Nonetheless, it is the consumer's sweetener of choice, to standard to which any synthetic alternative must compare. In sum, the ideal synthetic sweetener will taste like sucrose without any extra accompanying tastes or aftertastes. Saccharin, the most widely-used synthetic sweetener, is criticized by users for its undesirable bitter aftertaste. Similarly, the sweetener derived from the *Synsepalum dulcificum* berry is disliked for its non-sucrose-like lingering sweetness.

Another required characteristic of a synthetic sucrose substitute is non-toxicity. It was the suspicion of carcinoginicity which led to banning of the cyclamates, a once-popular group of sweeteners.

A class of sweeteners which has received good marks for non-toxicity are the dihydrochalcones. Initially, these materials were made by chemically modifying certain bitter components of several citrus fruits. Now, a variety of synthetically-derived materials have been proposed as well. These materials share a basic structure

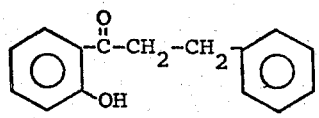

with a great variety of groups substituted into the two aromatic rings. As pointed out in Horowitz and Gentili's U.S. Pat. Nos. 3,087,821, issued Apr. 30, 1963, and 3,583,894, issued June 8, 1971, and amplified in their chapter in the book *Sweetness and Sweeteners*, Birch, Green, and Coulson, Eds., Applied Science Publ., Ltd., London, pp. 69–79 (1971), the exact nature of the substituents and their placement on the molecule are critical. A change which is minor on its face may have a major effect on the taste properties of the dihydrochalcone. Many of the dihydrochalcones prepared heretofore have menthol-like aftertastes and prolonged sweet aftertastes. Some dihydrochalcones disclosed by Farkus, Nogradi, Gollsegen and Antus in Hungarian Patent Application CI-1196, having a

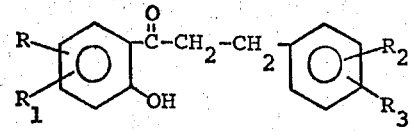

structure, wherein R is hydrogen, hydroxyl, alkoxyl, or substituted alkoxyl, $R_1$ is hydrogen or a "hydrophylous" group such as carboxyl, sulfonyl, or phosphonyl, and $R_2$ and $R_3$ are hydrogen or alkoxyls, which are chemically related to the present invention, have been evaluated and found to have unpleasant aftertastes. They pose a second problem, as well, in that their sweetness, relative to sucrose, is not immense. Although the best one is claimed to be 180 times as sweet as sugar, our tests indicate that this compound is only 76–81 times as sweet as sugar. Since the dihydrochalcones are relatively complex and likely expensive materials, it is desirable that a dihydrochalcone have a very high sweetening power, on the order of several hundred times that of sucrose on a pound for pound basis, so that the amount used may be reduced.

Another failing of many dihydrochalcone materials disclosed heretofore has been insufficient solubility in aqueous media. This can mean that a very sweet compound is not able to form solutions sweet enough to yield suitable consumer products.

STATEMENT OF THE INVENTION

A group of high solubility dihydrochalcones which have particularly desirable taste properties has now been discovered. These materials have the chemical structure

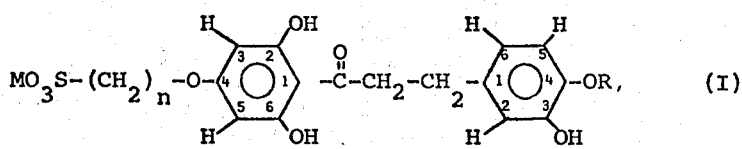

wherein M is a physiologically acceptable metal cation, n is 1, 2 or 3 and R is methyl, ethyl or propyl. These compounds have tastes characterized by sweetness and no appreciable aftertaste or companion taste. Compared to many dihydrochalcones proposed heretofore, they are very water-soluble so that intense sweet flavors can be generated.

DETAILED DESCRIPTION OF THE INVENTION

The Dihydrochalcones

In this Detailed Description, reference will repeatedly be made to the positions of various substituents on the dihydrochalcone molecule. These positions are numbered and will be referenced in accordance with General Formula (I).

The dihydrochalcones of this invention contain three hydroxyl groups at the 2, 6 and 3' positions. They contain hydrogen at the 3, 5, 2', 5', and 6' positions. At the 4' position they contain a lower saturated alkoxy group selected from the group of methoxy, ethoxy and the propoxies; preferably the 4'-substituent is a methoxy or n-propoxy, and most preferably a methoxy. At the 4 position they contain a substituted oxy group. This oxygen atom is substituted with an alkyl sulfonate anion to yield an oxyalkylsulfonate anion of from one to three carbon atoms inclusive. The alkyl sulfonate anion is present as a salt with a physiologically acceptable metal cation. As used herein, a "physiologically acceptable metal cation" is defined to include the cations of the third and fourth period metals which are non-toxic, i.e. Na I, K I, Mg II, Ca II, Al III, Mn II, Fe III, Cu II and Zn II. Preferred metal cations are the cations of the third and fourth period group I and II metals, i.e. Na I, K I, Mg II, and Ca II, with Ca II being the most preferred metal cation.

Preparation

The materials of General Formula I are conveniently formed, in a general sense, by the mechanism of alkylating the 7 hydroxyl group of the natural product hesperetin,

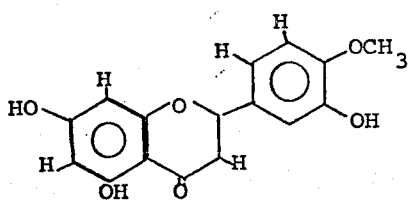

or a 4' ethoxy or propoxy equivalent of hesperetin with an alkyl sulfonate group and thereafter opening and reducing the alkylated hesperetin's flavanone structure to the corresponding dihydrochalcone by contacting the alkylated hesperetin with base under reducing conditions, for example, hydrogen plus a catalyst.

In the case when n in General Formula I equals 1, sodium iodomethanesulfonate or the pyrrolidine amide of chloromethylsulfenic acid are suitable agents with which to effect alklation. More specifically, hesperetin or a 4' ethoxy or methoxy equivalent can be reacted with the sodium salt of iodomethanesulfonic acid in the presence of potassium carbonate in DMF at reflux for several hours to yield at the 7 position of the hesperetin a sulfo-substituted methoxy. This material is then treated with the base under hydrogenation conditions as set forth above to open and reduce to the desired dihydrochalcone structure. Chloromethylsulfenyl chloride can be prepared when trithiane is contacted with molecular chlorine.

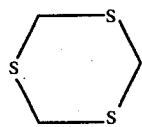

This product can be reacted with pyrrolidine,

to form

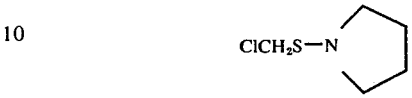

which will facilely alkylate hesperetin or the 4' ethoxy or propoxy equivalent in the 7 position and, after S oxidation and sulfonamide hydrolysis, yields a flavanone intermediate which can be hydrogenated and opened to the desired dihydrochalcone product.

In the case where n in General Formula I equals 2, the alkylating agent can be $Br-CH_2-CH_2-SO_3^-Na^+$, or the like. This material, when contacted with an equimolar amount of hesperetin or a 4' ethoxy or propoxy equivalent in the presence of potassium carbonate or a similar weak base, in DMF, DMSO, or the like, preferentially alkylates the 7 hydroxyl. There is, of course, as with all these reactions, some alkylation of other hydroxyls. The various materials may be separated by fractional crystallization or chromatography techniques.

In the case where n in General Formula I equals 3, propane sultone is the alkylating agent of choice, as it directly attaches the required 3 carbon alkyl group and the $SO_3^-$ in one step. This alkylation is carried out in DMF or DMSO or an equivalent dipolar aprotic solvent in the presence of carbonate or a like weak base. This alkylation is followed by the usual reduction and opening.

All of these alkylations can be carried out under relatively mild conditions, such as about room temperature for 24 to 72 hours. It is also possible to use elevated temperatures, such as up to about 100°C with corresponding shorter reaction times such as as short as about 1 hour.

The ring opening and reduction may be carried out in two steps-the opening brought about by contacting the alkylation product with a relatively strong base such as an aqueous alkali metal hydroxide solution for 0.2 to 4 hours at 10°C to 100°C; the hydrogenation being carried out with hydrogen gas and a catalyst such as a supported noble metal catalyst or the like at a temperature of from 10°C to 100°C for from 0.5 to 24 hours. Preferably the reduction and opening are carried out simultaneously with base, catalyst and hydrogen.

In an alternate preparative scheme, the dihydrochalcones are prepared by condensing an appropriate 2,6-dihydroxy-4-sulfoalkyloxy-acetophenone with an appropriate 3-hydroxy-4-alkoxy-benzaldehyde in the presence of base and then reducing. A typical reaction scheme is as follows:

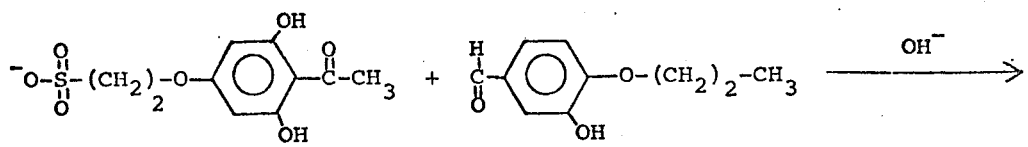

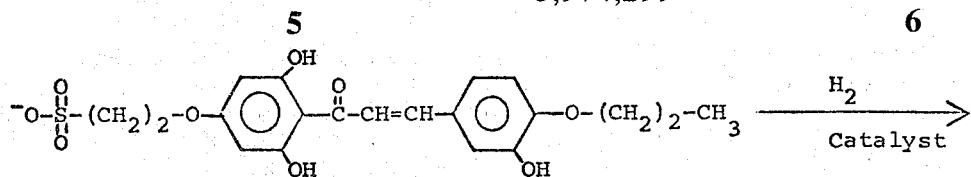

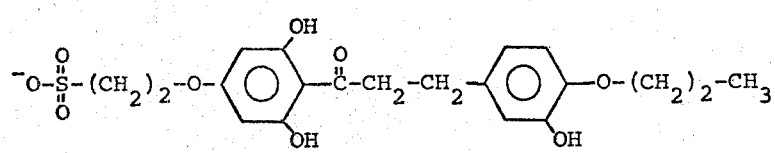

The condensation is effected under moderate conditions (10°–100°C for 24 to 1 hour) in the presence of strong base, such as alcoholic alkali metal hydroxide.

The products of any of these reactions can be purified and isolated by fractional crystallization, thin layer chromatography and the like, as desired.

The preparative schemes set forth have as their metal cations, the cation corresponding to the base used in the coupling or opening steps. By varying this base among NaOH, KOH, Ca(OH)$_2$ and the like a variety of metal cations can be incorporated. Also, it is possible to change cations by passage of a solution of dihydrochalcone over an appropriately charged ion exchange resin or often by merely adding an excess of the desired cation to a solution of dihydrochalcone and precipitating the desired salt.

These preparations will be further set forth in the examples. These are not intended to be limiting as other methods equivalent to those skilled in the art of organic synthesis may be employed as well.

Use of the Dihydrochalcones

These dihydrochalcones find application as sweeteners of consumable materials. In this use they are admixed with edible materials such as foods, beverages, medicines, and the like, in amounts effective for affording the degree of sweetness desired.

The dihydrochalcones represented by Formula I can be prepared in a variety of forms suitable for the utilization of sweetening agents. Typical forms which can be employed are: solid forms such as powders, tablets, and granules; and liquid forms such as solutions, suspensions, syrups and emulsions. These forms can consist of the compounds of the Formula I apart or in association with non-toxic sweetening agent carriers, i.e., non-toxic substances commonly employed in association with sweetening agents. Such suitable carriers include liquids such as water, ethanol, sorbitol, glycerol, citric acid, corn oil, peanut oil, soybean oil, sesame oil, propylene glycol, corn syrup, maple syrup and liquid paraffin; and solids such as lactose, cellulose, starch, dextrin and other modified starches, calcium phosphate and calcium sulfate. Obviously incompatible for use with the sweetening agents of Formula I would be toxic carriers such as methanol and dimethyl sulfoxide.

The dihydrochalcones are added to the edible composition by mixing methods known in the art. They may be used alone or as the primary or secondary sweetener in the final composition; with a natural sweetener such as sucrose, or another synthetic sweetener such as saccharin or cyclamate also being added.

Examples of specific edible materials which can be sweetened by the addition of a dihydrochalcone of Formula I or by a novel combination of the material of Formula I with a known sweetening agent include: fruits, vegetables, juices; meat products such as bacon and sausage; egg products; fruit concentrates; gelatins and gelatin-like products such as jelly and preserves; milk products such as ice cream, sour cream and sherbet; icings; syrups; grain products such as bread, cereals, pasta and cake mixes; fish; cheese products; nut products; beverages such as coffee, tea, non-carbonated and carbonated soft drinks, beers, wines and liquors; and confections such as candy and chewing gum.

Additional illustrations of the type of commercial products in which the sweetening agent or combinations thereof with known sweetening agents can be used are granulated mixes which upon reconstitution with water provide non-carbonated drinks; instant pudding mixes; instant coffee and tea; pet foods; livestock feed; tobacco and consumable toiletries such as mouth washes and toothpastes, as well as proprietary and non-proprietary pharmaceutical preparations.

The amount of dihydrochalcone employed can vary widely, just as the amount of natural sugar sweetener employed varies from person to person and food application to food application. As a general rule, the weight of dihydrochalcone added will be about 1/100–1/1000th the weight of sucrose required to yield the same sweetness. Thus, additions of from about 0.001% up to about 0.50% by weight (basis edible substance) may be usefully employed. The present materials offer the advantage that their solubility permits such addition to most food systems.

These dihydrochalcones, their preparation and their use are further described in the following Examples. These are to illustrate the invention and are not to be construed as limitations on this invention, which is instead defined by the appended claims.

EXAMPLE I

Preparation of

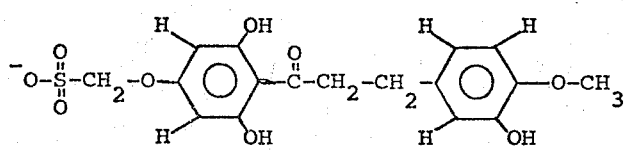

Following the general teachings of Douglass et al, *J. Org. Chem.* 15, 795–9 (1950), purified trithiane,

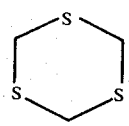

28 grams, and methylene chloride reaction solvent are placed in a vessel and chilled to 0°C. Chlorine gas (16 grams) is slowly passed into the vessel with stirring while maintaining the 0°C. temperature. After three hours, the vessel is permitted to warm to room temperature and unreacted chlorine is removed.

The reaction mixture is warmed to about 50°C and vacuum is applied, causing chloromethylsulfenyl chloride ($ClCH_2SCl$) to distill overhead.

Chloromethylsulfenyl chloride (one equivalent) is dissolved in benzene and two equivalents of pyrrolidine is gradually added with stirring. The mixture is stirred at room temperature for one hour. Benzene is stripped and a product,

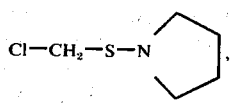 (VI), is isolated by distillation.

A solution of 3.0 g of hesperetin (Sigma Chemical Co.) in 20 ml of dimethylformamide is prepared. 0.7 Grams of anhydrous potassium bicarbonate is added followed by 4.6 g of VI. The mixture is stirred overnight, at which time excess peracetic acid is added in acetic acid solvent and stirred for 12 hours to form

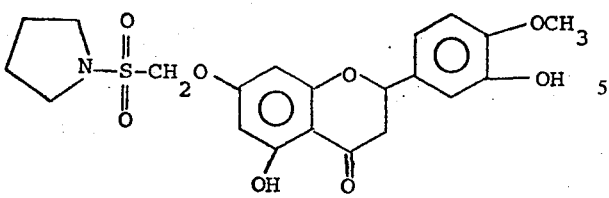

Water is then added and the mixture is stirred at room temperature for an hour to oxidatively hydrolyze and convert the sulfonamide to the sulfonate,

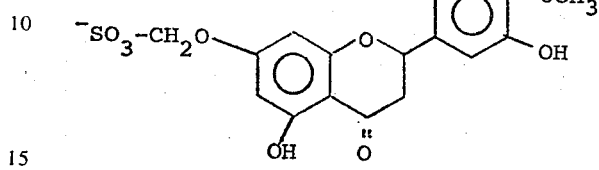

Sodium bisulfite is added to consume unreacted peracetic acid. Following evaporation of volatile materials, the sulfonate is obtained pure by crystallization from water. The sulfonate (1.5 grams) is dissolved in 30 ml of 5% aqueous KOH and placed in a 250 ml reaction flask with 250 mg of 5% palladium on charcoal. The reaction flask is flushed with hydrogen and the mixture is stirred at room temperature and about atmospheric pressure for about 35 hours. Thin layer chromatography analysis of the mixture before and after reaction indicates that there has been essentially quantitative reduction and opening of the flavanone ring to yield the desired compound, (compound 1a),

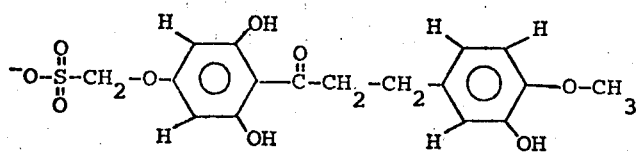

as the potassium salt.

This material is isolated following neutralization to pH 7–8 with HCl by concentration of the resultant solution in vacuo. After purification by recrystallization, analysis by NMR indicates that the product is the one desired compound.

To 452 mg (1.0 mmoles) of compound 1a in 10 ml of hot water is added 0.20 ml of 5m $CaCl_2$ solution (1.0mmoles). After warming, a precipitate forms which is the calcium salt, compound 1b. This is isolated and recrystallized.

EXAMPLE II

Preparation of

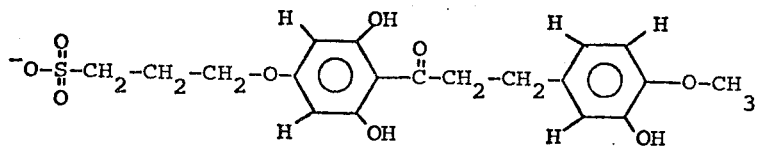

3.02 Grams of hesperetin, 1.38 grams of potassium carbonate and 1.22 grams of propane sultone

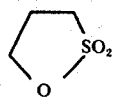

are placed in 40 ml of dimethylformamide and stirred overnight at room temperature. DMF is removed under vacuum leaving

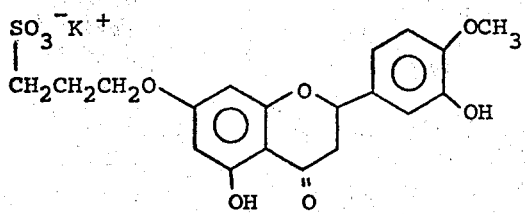

which is dissolved in 100 ml of 5% KOH and transferred to a hydrogenation vessel. Then 1 g of 5% palladium on charcoal is added, the mixture is flushed with argon, and then with hydrogen. Finally, it is pressured to 20 psig with hydrogen and shaken overnight. The mixture is filtered through Celite and brought to about pH 7–8 with hydrochloric acid. Water is removed under vacuum to yield a yellow solid. The solid is extracted with refluxing ethyl acetate, recrystallized from water to yield the desired product (product 2a) in pure form as the potassium salt. This product is converted to the calcium and zinc salts (products 2b and 2c) by the general method set forth in Example 1.

EXAMPLE III

Preparation of

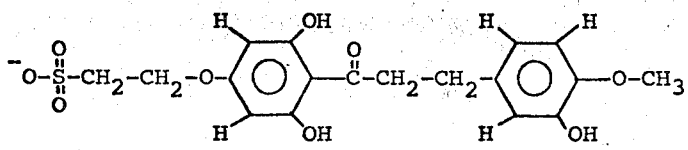

72 Milligrams of 50% sodium hydride is washed with hexane. 7 Milliliters of anhydrous dimethylsulfoxide is added under an argon cap. Next, 302 mg of hesperetin is slowly added in about one ml of dimethylsulfoxide. The mixture is reacted at room temperature and then at 50°C for about an hour. Then Br—CH$_2$—CH$_2$—SO$_3$Na (253 mg) in dimethylsulfoxide is added and the mixture is stirred overnight under argon at room temperature. Solvent is then stripped off and the product is extracted with ethylacetate. The residue is crystallized from water to purify and dissolved in 10 ml of 5% aqueous potassium hydroxide, 100 mg of palladium on charcoal and hydrogen (atmospheric pressure) are added and stirred overnight. The reaction product is filtered through Celite, brought to pH 7–8 with HCl and washed with ethylacetate. Water is stripped under vacuum to yield the desired potassium salt product, (product 3a).

EXAMPLE IV

Preparation of

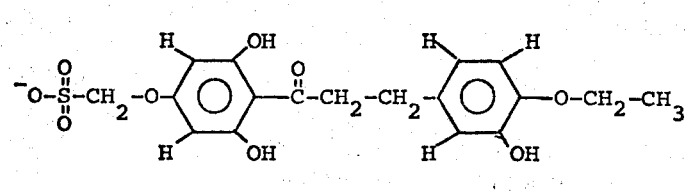

(product 4a)

and

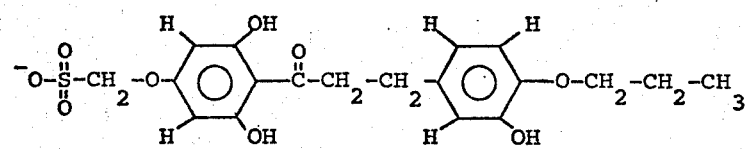

(product 4b)

Products 4a and 4b are prepared by condensing the appropriate benzaldehydes and acetophones as follows:

a. Preparation of Aldehyde Reactants

A solution of 2.76 g (20.0 mmoles) of 3,4-dihydroxybenzaldehyde and 2.76 g (20.0 mmoles) of anhydrous potassium carbonate and 3.45 g (22.0 mmoles) of ethyl iodide is prepared in 15 ml of dry DMF and stirred under argon for 24 hours at room temperature. The reaction mixture is poured into 50 ml of water, saturated with sodium chloride and extracted thrice with diethyl ether. The ether extracts are washed with water, and brine, dried and concentrated to yield the ethoxy aldehyde, 11 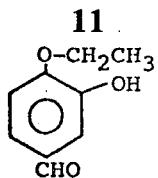   12 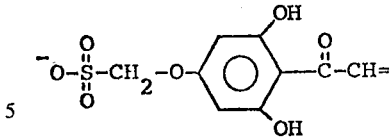

as dark crystals.

The reaction is repeated using 3.74 g (22.0 mmoles) of n-propyl iodide in place of ethyl iodide to yield the propoxy aldehyde,

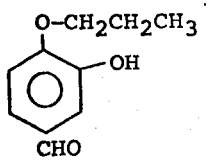

The process of this section b is repeated using the propoxy aldehyde of part a in place of the ethoxy aldehyde. The product which results has an NMR spectrum consistent with the propoxychalcone structure

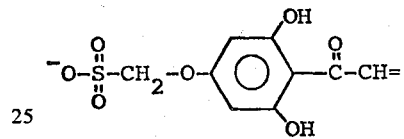

b. Coupling 1.5 Milliliters of 50% aqueous potassium hydroxide is added to a solution of 166 mg (1.0 mmole) of the ethoxy aldehyde of part a of this Example and 301 mg (1.0 mmole) of 2,6-dihydroxy-4-(sulfomethoxy) acetophenone

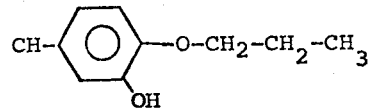

c. Reduction

A solution of 0.10 mmole of the ethoxychalcone in 1.0 ml of 5% KOH also containing 50 mg of 5% Pd on charcoal is placed in a flask and purged with hydrogen. The flask is capped and attached to a low pressure hydrogen source. The mixture is stirred for four hours at room temperature, filtered, and extracted with ethylacetate. The extract is dried and evaporated to give a material which crystallizes yielding a solid product 4a consistent with the dihydrochalcone structure

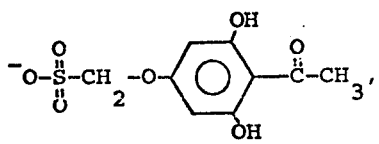

in 1.0 ml of absolute ethanol. The resultant mixture is stirred under argon at room temperature for 9 hours and then poured into 20 ml of 9% hydrochloric acid (ice cold) with stirring. A colored substance is extracted with this mixture when it is extracted twice with ether. The ether extracts are discarded. The aqueous solution was concentrated where upon off-white crystals were observed to form. This product has an NMR spectrum consistent with the ethoxychalcone structure

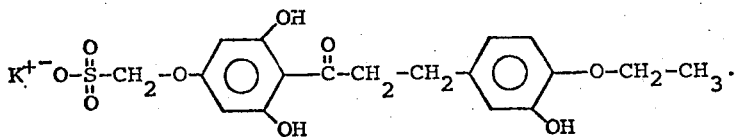

A portion of this material is dissolved in a solution of CaCl$_2$. The solution is evaporated and a precipitate forms. This precipitate is the calcium dihydrochalcone salt.

The reactions of this part are repeated with the propoxy material of part a and yield the propoxy-substituted dihydrochalcone (product 4b). This material is converted to the Ca II, Mg II, Na I, Fe III, and Zn II salts by the method set forth earlier in this section of this Example.

It would be possible to repeat this Example using methyl iodide, etc. to yield the methoxy substituted dihydrochalcone,

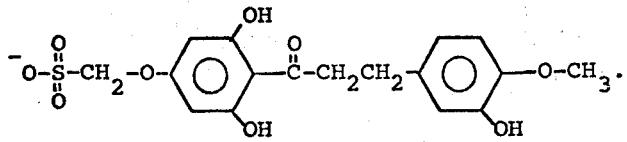

However, in view of the ready availability of the natural product, hesperetin, as a route to methoxy dihydrochalcone, this route is generally not preferred.

EXAMPLE V

Preparation of with step b of Example IV but with 2,6-dihydroxy-4-sulfoethoxy-acetophenone instead of the methoxy material employed in Example IV. The products are reduced as in step c of Example IV to yield products 5a and 5b. These materials are converted to a variety of physiologically acceptable metal salts by the process of step c of Example IV. As before, the methoxy equivalents of the ethoxy and propoxy materials could also be produced by this process, if desired.

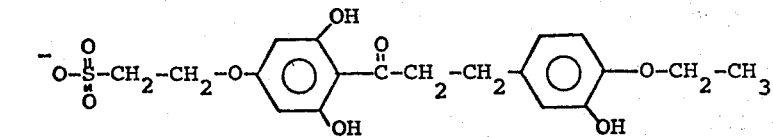

(product 5a)

and

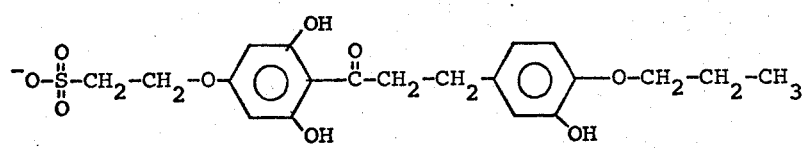

(product 5b)

The process of Example IV is repeated twice. The ethoxy and propoxy aldehydes of part a of Example IV are prepared. They are in turn reacted in accordance

EXAMPLE VI

Preparation of

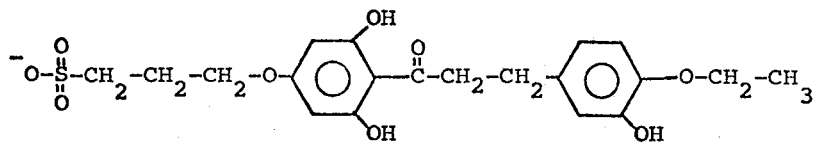

(Product 6a)

and

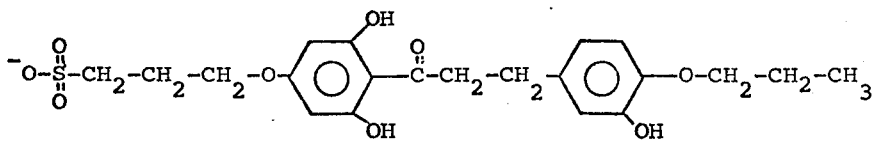

(product 6b)

The process of Example IV is repeated twice more. The aldehydes of part a of Example IV are prepared and reacted in accordance with step b of Example IV but with 2,6-dihydroxy-4-sulfopropoxy-acetophenone instead of the 4-methoxy material employed in Example IV. The products are reduced as in step c of Example IV to yield products 6a and 6b. These materials are converted to a variety of physiologically acceptable metal salts by the method set forth in Example IV.

EXAMPLE VII

This example shows an alternate preparation of 1-(2,3′,6-trihydroxy-4′-methoxy-dihydrochalcone-4-oxy) ethane-2-sulfonate salts

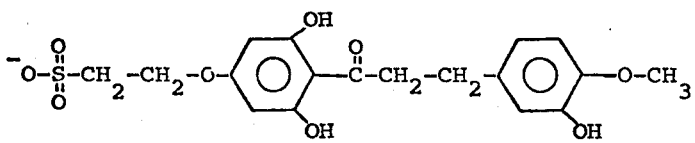

a. preparation of 3′,5-Dihydroxy-4′-Methoxy-7-Bromoethoxy-Flavanone (material 7a)

A solution-suspension of 1.73 g (12.5 mmoles) of anhydrous potassium carbonate, 3.02 g (10.0 mmoles) hesperetin and 18.8 g (100 mmoles) dibromethane in 100 ml DMF is stirred vigorously under argon at 42°C for 15 hours. The reaction mixture is then poured into 600 ml of water and extracted with ethyl acetate (3 × 75 ml), the combined portions of which are washed with water (3 × 75 ml), brine (1 × 75 ml), hen dried over MgSO$_4$ and concentrated yielding 8.74 g of an oily yellow solid. Tlc (silica gel F-254, CH$_2$Cl$_2$—CH$_3$OH 95:5) indicates a rough ratio of product (R$_f$=0.58) to starting material (R$_f$=0.10) of 2:1 as well as at least five other unknown minor impurities. The crude product is then heated to boiling with 50 ml ether. After cooling, the mixture is filtered yielding 1.01 g of product (homogeneous on tlc) as an off-white solid. The filtrate is concentrated and recycled. After three cycles, 2.01 g (50%) of the pure bromoethyl derivative is obtained. Recrystallization from hexane-chloroform gives white clusters having a mp of 153°–4°C and infrared and NMR spectra consistent with material 7a.

b. Preparation of 2,3′,6-Trihydroxy-4-Bromoethoxy-4′-Methoxy-Chalcone (material 7b)

Ten ml of 5% KOH is added to 400 mg (1.00 mmole) of 3′,5-dihydroxy-4′-methoxy-7-bromoethoxy-flavanone giving a bright yellow solution which is stirred under argon at ambient temperature for 2 hours. The reaction mixture is then poured into 100 ml of water, acidified with 10% HCl, and extracted immediately with ethyl acetate (2 × 25 ml). The combined extracts are washed with dilute NaHCO$_3$ (1 × 25ml), dried over MgSO$_4$ and concentrated yielding 0.51 g of a partially crystalline orange oil. Tlc (silica gel F-254, CH$_2$Cl$_2$—CH$_3$OH 95:5), indicates the reaction to have proceeded nearly quantitatively showing only the product (R$_f$=0.28) and a barely observable spot for starting material (R$_f$=0.73). Preparative tlc on silica gel PF-254, eluting with CH$_2$Cl$_2$—CH$_3$OH 95:5, yielded 302 mg (75%) of the chalcone as a yellow solid. Recrystallization from hexaneethyl acetate gives orange clusters having mp 158°–162°C and spectra consistent with material 7b.

c. Preparation of 2,3′,6-Trihydroxy-4-Bromoethoxy-4′-Methoxy-Dihydrochalcone (material 7c)

Sixty mg of 10% Pd—C is added to a degassed solution of 88 mg (0.22 mmole) of 2,3',6-trihydroxy-4-bromoethoxy-4'-methoxy-chalcone in 30 ml of ethyl acetate. The resultant mixture is shaken on a Parr hydrogenation apparatus at an initial H₂ pressure of 31 lb. After 1 hour, the reaction mixture is filtered through Celite and concentrated yielding 92 mg (100%) of an off-white oil. Tlc (silica gel F-254, $CH_2Cl_2$—$CH_3OH$ 95:5) indicates the reduction to be quantitative showing only one spot having $R_f$=0.28. The crude product solidifies into a hard foam under vacuum, but resists several attempted recrystallizations. Infrared and NMR spectra are consistent with structure 7c.

d. Preparation of Potassium 1-(2,3',6-Trihydroxy-4'-methoxy-dihydrochalcone-4-oxy) Ethane-2-Sulfonate To a solution of 0.90 g (2.24 mmoles) 2,3',6-trihydroxy-4-bromoethoxy-4'-methoxy-dihydrochalcone in 10 ml of methanol is added a solution of 396 mg (2.50 mmoles) $K_2SO_3$ in 10 ml water. On brief heating, a homogeneous reaction mixture is obtained that is refluxed overnight. The hot solution is then filtered through Celite and concentrated giving 1.54 g of a slightly wet white solid. Tlc on silica gel F-254 (saturated with water), eluting with n-butanol (saturated with water) shows one main spot ($R_f$=0.41) in addition to six minor impurities. Recrystallization of the crude product from either water or methanol-water mixtures is difficult, although a 28 mg sample of pure sulfonate is obtained in this way. This material (product 7a) had mp of 178°–185°C without decomposition. A portion of this material is contacted with aqueous Ca II to yield the equivalent Ca II salt which is also isolated (product 7b).

EXAMPLE VIII

This example illustrates an alternate preparation of 1-(2,3',6-trihydroxy-4'-methoxy-dihydrochalcone-4-oxy) propane-3-sulfonate salts, pure alkylation product as an off-white solid. This material is dissolved in 100 ml of 5% KOH to give a yellow solution which is shaken overnight with 1.0 g of 5% Pd–C at 24 lb. initial hydrogen pressure. The reaction mixture is then filtered through Celite and neutralized with HCl. The resultant solution is concentrated to a volume of ca. 150 ml and allowed to stand overnight, whereupon 1.46 g of white clusters separates. Concentration of the mother liquor yields an additional 1.17 g of material for a total yield of 2.63 g (55%). Tlc analysis (as above) of this product indicates only one component having a $R_f$=0.67 and which has spectra and an elemental analyses consistent with product 8a.

b. Preparation of Sodium Salt of 1-(2,3',6-Trihydroxy-4'-Methoxy-dihydrochalcone-4-oxy) Propane-3-Sulfonic Acid (product 8b)

Amberlite 120 resin (125 cc) is placed in a column and eluted with 1 N NaOH solution until the effluent shows a pH 9. After the resin has been rinsed to neutrality with deionized water, a solution of 464 mg (1.00 mmole) of the potassium salt (product 8a) is applied to the column and eluted with water at a rate of 1.4 ml/min until no sweetness is detected in the effluent. The resultant aqueous solution is freeze-dried to give 492 mg of white solid (product 8b).

c. Preparation of Calcium Salt of 1-(2,3',6-Trihydroxy-4'-Methoxy-dihydrochalcone-4-oxy) Propane-3-Sulfonic Acid (product 8c)

To a solution of 464 mg (1.00 mmole) of the potassium salt (product 8a) in 10 ml hot water is added 0.20 ml of 5 M CaCl₂ solution (1.00 mmole). On warming briefly a precipitate forms that is filtered and then recrystallized from 50 ml water yielding 320 mg (47%) of white solid (product 8c).

EXAMPLE IX

This example sets forth taste evaluations made on certain of the products of Examples I through VIII to

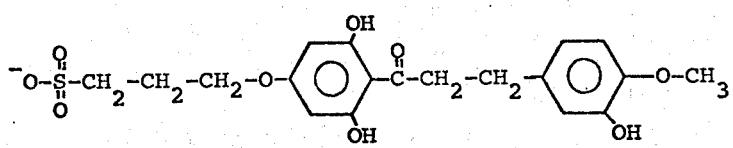

a. Preparation of 1-(2,3',6-Trihydroxy-4'-Methoxy-Dihydrochalcone-4-oxy) Propane-3-Sulfonic Acid, Potassium Salt (product 8a)

To a solution of 3.02 g (10.0 mmoles) of hesperetin and 2.44 g (20 mmoles) of propane sultone in 40 ml DMF is added 1.38 g (10.0 mmoles) of anhydrous K₂CO₃. The resulting reaction mixture is stirred at ambient temperature for 3 days. The reaction is then checked by tlc (Eastman Chromagram 13254 Cellulose, HOAc-H₂O-i-BuOH 1:1:2) and found to contain mainly one product (I₂ staining and uv visualization) having $R_f$=0.68 along with a small amount of starting material. The DMF is then removed at reduced pressure and the residue taken up in 25 ml water. This mixture is then extracted with EtOAc (4 × 15 ml) to remove unreacted hesperetin and propane sultone. The aqueous solution is then concentrated to yield the neardetermine their sweetness relative to sucrose and their sweetness parity, i.e. percentage of sweet taste, bitter taste, sour taste and salty taste. Conventional sweeteners were tested as well.

The tests were carried out by a team of food technologists in an independent testing laboratory. Six judges were selected from a panel of individuals trained and screened in their ability to differentiate minor differences in taste.

The tests were conducted in a series of sessions using the following methods:

Sample Preparation

The amount of sucrose or sweetener required to give the desired concentration in solution was weighed on tared paper, transferred to a volumetric flask and the paper reweighed to be sure of complete transfer. The sample was then dissolved in distilled, charcoal-filtered

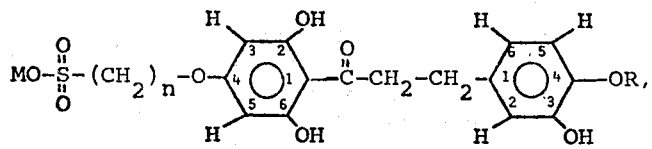

water and brought to volume. Samples were served at room temperature (20°C ± 2°C).

Four concentrations of sucrose or sweetener were tested at each session. Four subjects evaluated sucrose at 11:00 AM and the blended sweeteners at 2:30 PM. Two subjects tested them at 10:30 AM and 11:30 AM due to scheduling difficulties. Each judge received 5 replications of each of the 4 concentrations at each session. Twenty 1 oz. plastic cups coded with 3 digit random numbers containing approximately 15 ml of each sample were randomly placed on a plastic turntable before the subjects arrived.

Test Procedure

Prior to testing, each judge was given a beaker containing reference solution (sucrose of known concentration) to be assigned a value of "10". After familiarizing himself with the reference, the subject returned the beaker and began to taste the samples on the turntable. He was asked to give a number representing the sweetness intensity of the sample relative to the reference.

Breadsticks and distilled, charcoal-filtered water were used to eliminate or lessen flavor carry-over between samples. Sample order was randomized by sample placement on the turntable and by rotation of the turntable between samplings.

Data Analysis

The numbers generated by the panel were analyzed using a computer program written specifically for magnitude estimation experiments. The input consists of the sweetener concentrations and subject responses. Its output is an equation of the line for the logarithm of perceived intensity vs the logarithm of stimulus concentration. It is possible to compare the sweetness intensity of sucrose to the test compound by determining the perceived intensity of a given concentration of sucrose and finding the concentration of test compound required to duplicate that intensity.

The results of these tests are summarized in the accompanying table, Table I. These results show that the products of this invention have highly intense sweetness often 500 times or more that of sucrose. Also, the present materials have a very pure sweet taste, i.e. low amounts of bitterness, etc..

wherein $R$ is a lower alkyl of from one to three carbon atoms inclusive, $n$ is an integer of from one to three inclusive and $M$ is a physiologically acceptable metal cation.

2. The dihydrochalcone compound of claim 1, wherein $n$ has a value of 1 and $R$ is methyl.

3. The dihydrochalcone compound of claim 1, wherein $n$ has a value of 1 and $R$ is ethyl.

4. The dihydrochalcone compound of claim 1, wherein $n$ has a value of 1 and $R$ is n-propyl.

5. The dihydrochalcone compound of claim 1, wherein $n$ has a value of 2 and $R$ is methyl.

6. The dihydrochalcone compound of claim 1, wherein $n$ has a value of 2 and $R$ is ethyl.

7. The dihydrochalcone compound of claim 1, wherein $n$ has a value of 2 and $R$ is $n$-propyl.

8. The dihydrochalcone compound of claim 1, wherein $n$ has a value of 3 and $R$ is methyl.

9. The dihydrochalcone compound of claim 1, wherein $n$ has a value of 3 and $R$ is ethyl.

10. The dihydrochalcone compound of claim 1, wherein $n$ has a value of 3 and $R$ is $n$-propyl.

11. The compound of claim 2, wherein $M$ is potassium ion.

12. The compound of claim 2, wherein $M$ is calcium ion.

13. The compound of claim 5, wherein $M$ is potassium ion.

14. The compound of claim 5, wherein $M$ is calcium ion.

15. The compound of claim 8, wherein $M$ is potassium ion.

16. The compound of claim 8, wherein $M$ is calcium ion.

17. A sweetened consumable material comprising an edible material and, as a sweetening agent, a dihydrochalcone compound of claim 1 in the amount which will afford the degree of sweetness desired.

TABLE I

| Test Materials | Sweetness Intensity times Sweetness of Sucrose | Flavor Make Up | | | | |
|---|---|---|---|---|---|---|
| | | % Sweet | % Sour | % Salty | % Bitter | % Other |
| Product 7a | 705 | 83 | 1 | 3 | 7 | 6 |
| Product 7b | 557 | 84 | — | 2 | 7 | 6 |
| Product 8a | 420 | 88 | 4 | 1 | 3 | 3 |
| Product 8c | 407 | 82 | — | 4 | 9 | 5 |
| Aspartame | 106 | 77 | 2 | 6 | 15 | — |
| Saccharin | 387 | 87 | 0 | 8 | 4 | 1 |

We claim:

1. A dihydrochalcone compound represented by the structural formula

* * * * *